United States Patent [19]

McAvinn et al.

[11] 4,163,896
[45] Aug. 7, 1979

[54] WET DRESSING HEATING SYSTEM

[75] Inventors: James D. McAvinn, Chicago; Harish A. Patel, Crystal Lake, both of Ill.

[73] Assignee: The Kendall Company, Boston, Mass.

[21] Appl. No.: 811,026

[22] Filed: Jun. 29, 1977

[51] Int. Cl.² .............................................. H05B 3/58
[52] U.S. Cl. ................................... 219/525; 422/307; 38/71; 128/254; 128/403; 219/386; 219/521; 219/527; 219/528
[58] Field of Search ............... 219/243, 245, 386, 387, 219/521, 524, 525, 527, 528, 530, 549, 211, 212, 213; 128/254, 399, 400, 403; 38/66, 71; 57/34; 21/91

[56] References Cited

U.S. PATENT DOCUMENTS

| 1,455,696 | 5/1923 | Wright | 219/527 X |
|---|---|---|---|
| 1,474,833 | 11/1923 | Hauptman | 38/71 X |
| 1,498,654 | 6/1924 | Hauptman | 38/71 |
| 1,498,655 | 6/1924 | Hauptman | 38/71 X |
| 1,594,053 | 7/1926 | Evans | 219/527 |
| 1,653,901 | 12/1927 | Haessly | 128/256 |
| 1,950,498 | 3/1934 | Lehnen et al. | 38/71 |
| 2,162,021 | 6/1939 | Kidwell | 219/527 UX |
| 2,198,989 | 4/1940 | Cooley | 128/254 |
| 2,317,406 | 4/1943 | Ryan | 38/71 |
| 2,363,735 | 11/1944 | Lord | 219/527 |
| 2,590,212 | 3/1952 | Samuels | 128/254 |
| 3,068,598 | 12/1962 | Johnston | 38/71 |
| 3,290,807 | 12/1966 | Esaka | 38/71 |
| 3,555,711 | 1/1971 | Mikkelsen | 38/71 |
| 3,746,837 | 7/1973 | Frey et al. | 219/525 X |
| 3,879,171 | 4/1975 | Tulis | 21/91 |

FOREIGN PATENT DOCUMENTS

| 373748 | 4/1923 | Fed. Rep. of Germany . |
|---|---|---|
| 372768 | 5/1932 | United Kingdom . |
| 602504 | 3/1948 | United Kingdom . |
| 725665 | 3/1955 | United Kingdom . |
| 770295 | 3/1957 | United Kingdom . |
| 908827 | 10/1962 | United Kingdom . |
| 1058549 | 2/1967 | United Kingdom . |
| 1063245 | 3/1967 | United Kingdom . |
| 1123752 | 8/1968 | United Kingdom . |

Primary Examiner—Volodymyr Y. Mayewsky
Attorney, Agent, or Firm—Powell L. Sprunger

[57] ABSTRACT

A heating system for dressings comprising a housing having a pair of opposed heating elements. The housing may be opened to place the dressings intermediate the heating elements, and may be closed in order to heat the dressings intermediate the elements.

15 Claims, 8 Drawing Figures

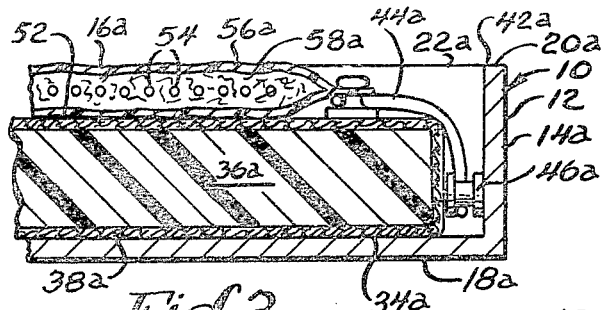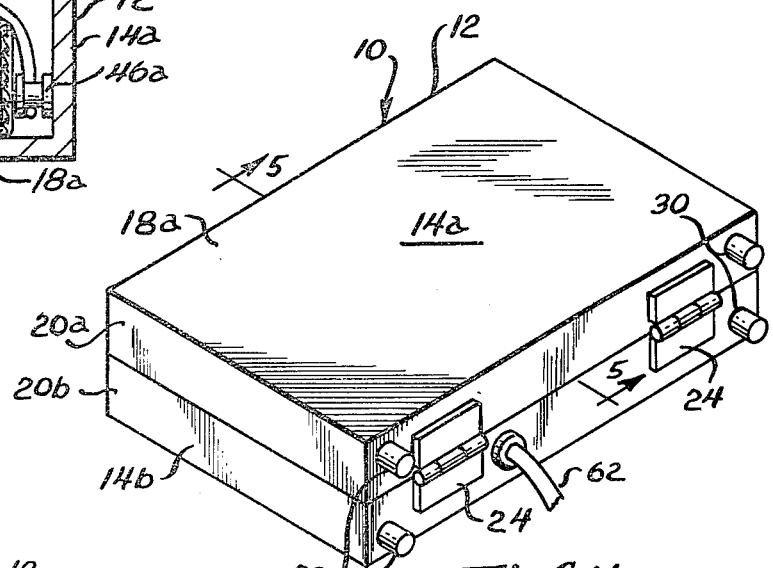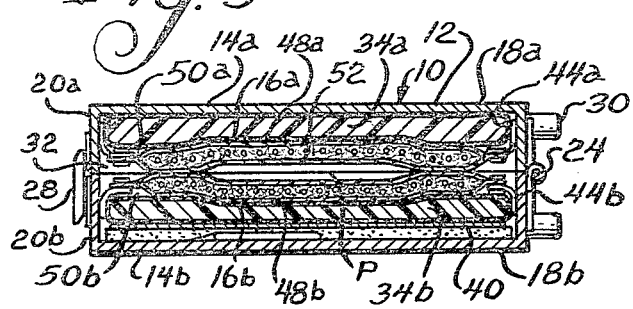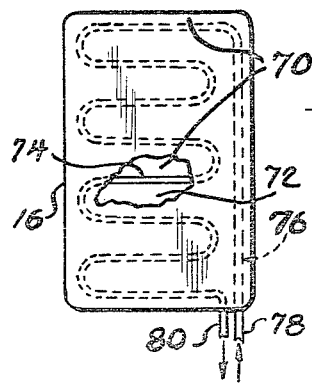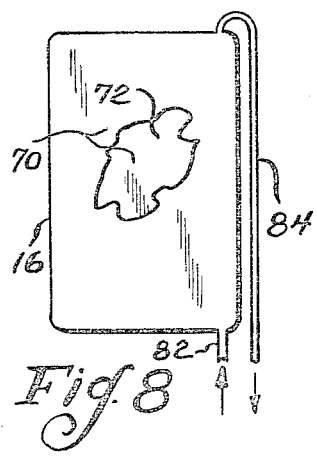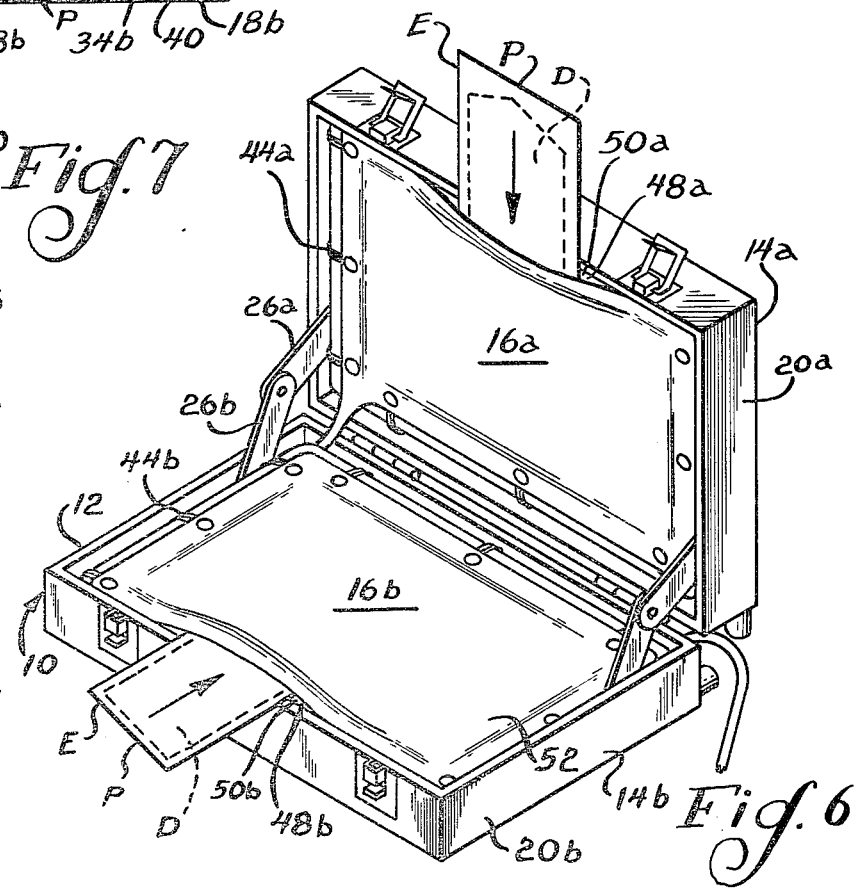

WET DRESSING HEATING SYSTEM

BACKGROUND OF THE INVENTION

The present invention relates to heating systems, and more particularly to such systems for heating wet dressings.

Wet dressings are commonly used for therapeutic purposes, such as on abscesses and boils. The wet dressings are applied in a heated state and serve to prevent tissue encrustation, and promote localized blood flow and fluid drainage, with the effect of reducing swelling and its consequent pain. Such dressings are commonly packaged in specially designed foil packs which are capable of conducting and withstanding increased temperatures and internal pressures during heating. After appropriate heating, the dressings are removed from the packs, and are applied to the patient.

In the past, the dressings are commonly heated through use of radiant heating procedures. Thus, the packed dressings may be stacked below a bulb which emits infrared rays in order to heat the dressings in the foil packs. The upper pack of the stacked packs remains below the heating bulb for a set period of time, such as five minutes, after which the upper pack may be removed and the underlying packs must be sequentially heated for additional periods of time, such as three minutes each. Thus, such prior devices require an extended period of time in order to heat a series of wet dressings, and limit immediate access to a plurality of heated dressings. Moreover, the heating device does not permit storage of dressings in a heated condition, and the dressings must be applied immediately after heating in order to prevent their cooling prior to use. Further, one or more of the wet dressings may be overheated due to lack of precise control over the radiant heating procedure, resulting in possible discomfort and harm to the patient when applied to the patient's tissue. In addition, the number of dressings which may be simultaneously heated is limited by the capabilities of the heating device.

SUMMARY OF THE INVENTION

A principal feature of the present invention is the provision of a system for heating wet dressings in an improved manner.

The heating system of the present invention comprises, a housing having a pair of first and second closure shells, with each of the shells having a back wall and sidewalls extending around the periphery of the associated back wall, and with the back wall and sidewalls defining a cavity in each of the shells. The system has hinge means connecting a sidewall of the first and second shells and permitting movement of the shells between a first open position of the housing and a second closed position of the housing with the sidewalls of the shells mating and with the shells defining a closed chamber. The system has first and second heating elements, and means for supporting the heating elements in the housing with the first heating element being located adjacent outer edges of the sidewalls in the first shell and substantially closing the cavity in the first shell, and with the second heating element being located adjacent outer edges of the sidewalls in the second shell and substantially closing the cavity in the second shell. The heating elements closely face each other in the second housing position such that they define a heating space intermediate the heating elements of the closed housing, and the heating elements are widely spaced in the first housing position for receipt of the dressings intermediate the heating elements. The heating elements are at least partially free of attachment and define an access opening adjacent an outer end of the respective shell relative the hinge means. The system has first and second insulation members in the housing, with the first insulation member being located intermediate the first heating element and the back wall of the first shell and defining a narrow storage space intermediate the first heating element and first insulation member, and with the second insulation member being located intermediate the second heating element and the back wall of the second shell and defining a narrow storage space intermediate the second heating element and second insulation member.

A feature of the present invention is that the housing may be readily opened to its first position in order to place a plurality of wet dressings intermediate the heating elements.

Another feature of the present invention is that the housing may be closed, and the plural dressings may be simultaneously heated intermediate the closely spaced heating elements of the closed housing.

A further feature of the invention is that the dressings may be heated to a selected temperature in order to prevent overheating of the dressings.

Still another feature of the invention is that the heated dressings may be removed from the heating space and placed into the storage spaces for subsequent use.

Yet another feature of the invention is that the dressings are maintained at the selected temperature in the storage spaces.

Thus, a feature of the invention is that a number of dressings may be heated and stored at a precisely controlled temperature over a period of time until desired for use.

A further feature of the present invention is that the system minimizes the amount of heat loss during heating of the dressings.

Further features will become more fully apparent in the following description of the embodiments of this invention and from the appended claims.

DESCRIPTION OF THE DRAWINGS

In the drawings:

FIG. 3 is a fragmentary sectional view taken substantially as indicated along the line 3—3 of FIG. 1;

FIG. 4 is a perspective view of the heating system of FIG. 1 illustrating the housing in a closed configuration;

FIG. 5 is a sectional view taken substantially as indicated along the line 5—5 of FIG. 4;

FIG. 6 is a perspective view illustrating the heating system in an open configuration during placement of heated dressings into storage spaces in the system; and FIGS. 7 and 8 are plan views, partly broken away, of alternative heating elements for the heating system of the present invention.

DESCRIPTION OF THE PREFERRED EMBODIMENTS

Figure 1:
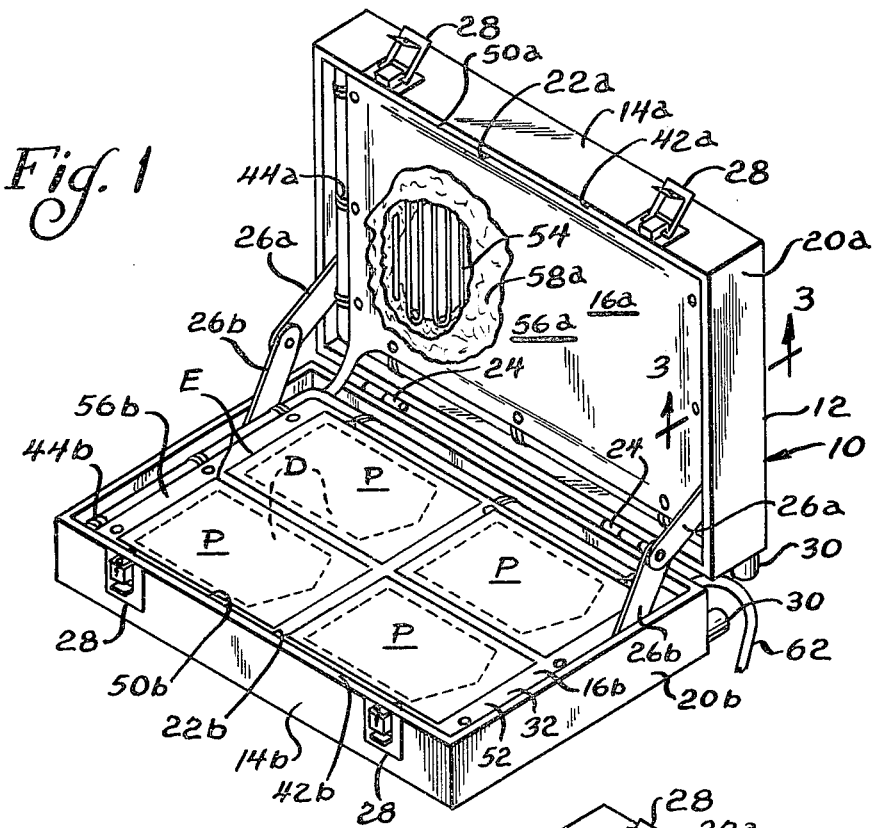
FIG. 1 is a perspective view, partly broken away, of a heating system of the present invention illustrating a housing of the system in an open configuration.

Referring now to FIGS. 1-5, there is shown a heating system generally designated 10 having a housing 12 comprising a pair of opposed first and second shells 14a and 14b and opposed first and second heating elements 16a and 16b. As shown, each of the shells 14a and b has a respective back wall 18a and 18b, and sidewalls 20a and 20b extending around the periphery of the associated back wall 18a and b, with the back walls 18a and b and respective sidewalls 20a and b defining an associated cavity 22a and b in the shells. The housing 12 has a pair of hinges 24 connected between inner sidewalls of the shells 14a and b, such that the housing shells 14a and b may be moved between a first open position, as illustrated in FIG. 1, and a second closed position, as illustrated in FIG. 4. With reference to FIG. 1, the housing 12 has a pair of pivoted connected links 26a and 26b extending from the sides of the opposed shells 14a and b in order to limit movement of the shells away from each other at the first housing position. The housing 12 also has a pair of locking members 28 of known type in order to releasably lock the shells 14a and b together at the second housing position, as illustrated in FIG. 5. The housing 12 may also have a plurality of resilient bumpers or support members 30 extending outwardly from the inner side walls of the shells 14a and b to provide support for the housing when placed in an upright configuration in its closed second position. It will be seen in connection with FIGS. 4 and 5 that the sidewalls 20a and b of the respective shells 14a and b mate with each other when the housing is in its closed second position, such that the shells 14a and b define a closed chamber 32 in the housing. The housing may be made of any suitable material, such as plastic or metal, as desired.

Figure 2:
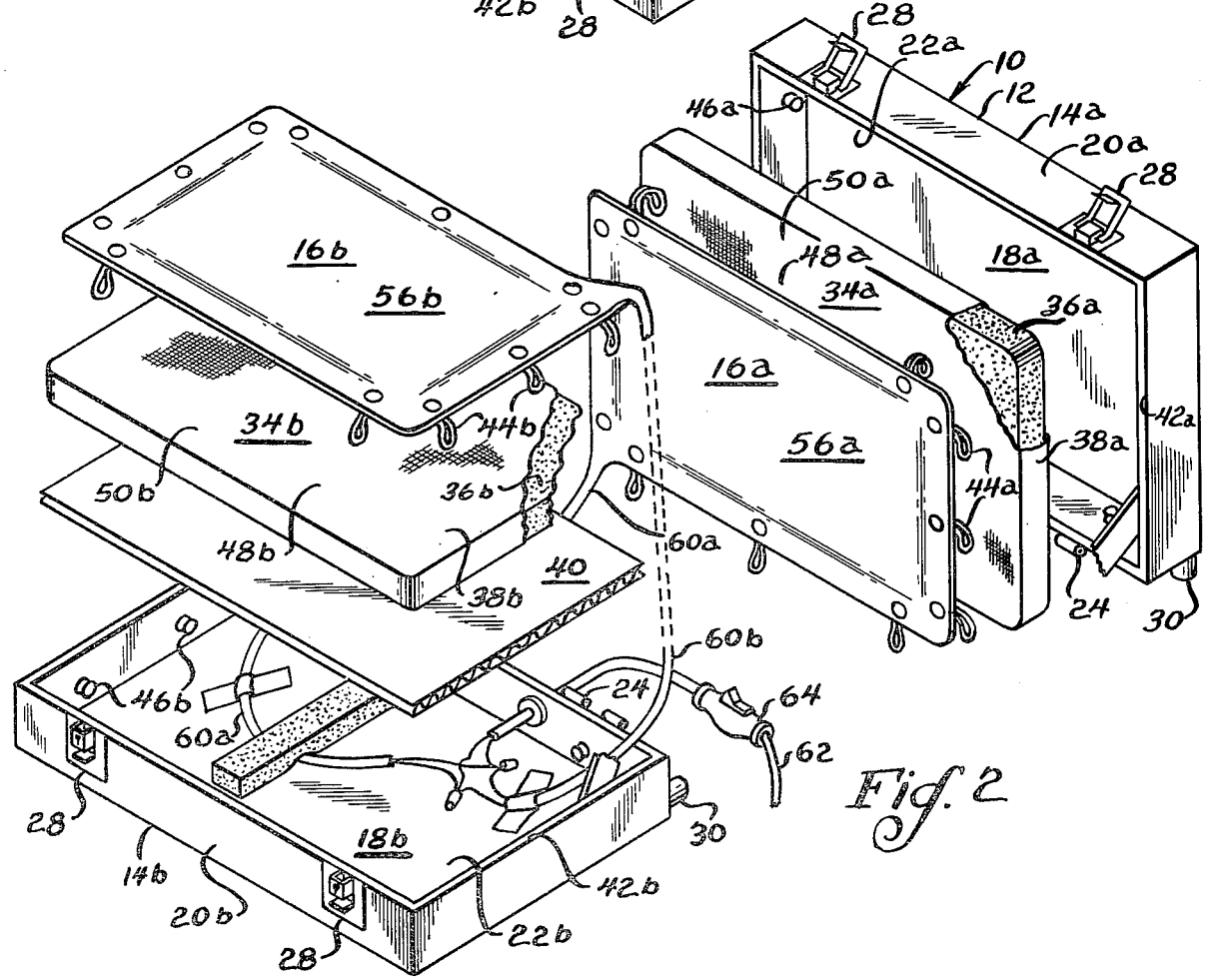
FIG. 2 is an exploded view, partly broken away, of the heating system of FIG. 1.

With reference to FIGS. 2, 3, and 5, the heating system 10 has a pair of opposed insulation members 34a and 34b adjacent the back walls 18a and b which may be made of any suitable material, such as inner foam sheets 36a and 36b covered by a suitable fabric or sheets 38a and 38b. As shown, the insulation members 34a and b preferably have dimensions approximately equal to the dimensions of the shell cavities 22a and b, such that they cover the back walls 18a and b of the respective shells 14a and b. One or both of the insulation members 34a and b may be spaced slightly from the associated shell back wall 18a or b by a sheet 40 of suitable material which covers and protects wiring in the housing, as best shown in FIGS. 2 and 5.

With reference to FIGS. 1-3, and 5, the first and second heating elements 16a and b substantially span the associated shell cavities 22a and b, and are located adjacent outer edges 42a and 42b of the respective shell sidewalls 20a and b in a configuration overlying the respective insulation members 34a and b. The heating elements 16a and b may be secured in place by any suitable means, such as a plurality of associated elastic loops 44a and 44b connected between the respective heating elements 16a and b, and inwardly directed bosses 46a and 46b spaced around the respective shell sidewalls 20a and b, as best shown in FIG. 3. The elastic loops 44a and b interconnect the heating elements 16a and b to the associated housing shells 14a and b, and bias the back side of the heating elements 16a and b against the outer face of the respective insulation members 34a and b. Thus, the heating elements 16a and b contact the associated insulation members 34a and b, and defined a storage space or compartment 48a and 48b intermediate the respective heating elements 16a and b and insulation members 34a and b. Also, as best shown in FIGS. 1 and 2, the elastic loops 44a and b are spaced from each other a substantial distance along the outer edge of the heating elements 16a and b, i.e., adjacent the locking members 28, such that the outer edges of the heating elements 16a and b are free of attachment from the housing shells 14a and b, and define access openings 50a and 50b adjacent the outer ends of the respective housing shells 14a and b which communicate with the respective storage spaces 48a and b. Thus, the elastic loops 44a and b may be expanded slightly in order to move the heating elements 16a and b away from the respective insulation members 34a and b and facilitate placement of heated dressings through the access openings 50a and b into the storage spaces 48a and b.

The front surfaces of the heating elements 16a and b face each other in the closed housing, as shown in FIG. 5, and define a relatively narrow heating space 52 when the housing is in its second closed position. In a preferred form, as shown, the front faces of the heating elements 16a and b in the closed housing contact each other and compress against the dressings during heating. Thus, with reference to FIG. 1, the housing 12 may be moved to its open position with the heating elements 16a and b widely spaced from each other, such that a plurality of wet dressing packs P may be placed on the outer surface of a heating element, such as the heating element 16b, as shown. The housing may be moved to its second closed position where the heating elements bear upon and compress the dressing packs P intermediate the heating elements 16a and b in the heating space 52.

The heating elements may be of any suitable type having electrically conductive heating members or cores 54 extending substantially throughout the heating elements 16a and b between respective outer fluid impervious covers 56a and b which define the front and back surfaces of the respective heating elements 16a and b. The heating elements 16a and b preferably have elastic pad members 58a and 58b separating the opposed walls of the flexible covers 56a and b, such that the heating elements 16a and b are sufficiently flexible and elastic to yield slightly during compression of the dressing packs intermediate the heating elements 16a and b in the closed position of the housing 12. In a suitable form, the heating elements 16a and b may comprise separate heating pads, Model H-9000, sold by Essex International, Inc., Belton, S.C.

With reference to FIG. 2, the heating member of heating element 16b is electrically connected to the heating member of heating element 16a by suitable electrically conductive wires 60a and b, and the interconnected heating members of the heating elements 16a and b are electrically connected to a power supply wire 62 having a suitable plug (not shown) which may be attached to a power source outlet providing a source of electrical current for the heating members, such that the electrical current passing through the connected heating members results in generation of heat. The connecting wire 62 may have a suitable On-Off switch 64 in order to control the selective passage of electrical current to the heating members and control the heating condition of the system 10. The heating elements are thermostatically controlled at a temperature in a temperature range desired for the dressings, such as 115°–120° F., and the system may have a suitable device of known type to control and modify the temperature generated by the heating elements 16a and b at a selected temperture in the range.

The dressing packs P are of known type and may have moist dressings D located between outer fluid impervious foil envelopes E for maintaining the dressings D in a moist condition prior to use. With reference to FIG. 1, the shells 14a and b are moved to the open first position of the housing 12, and, as previously described, a plurality of dressing packs P may be placed on one of the heating elements 16a or b. The housing 12 may then be moved to its closed second position, as shown in FIG. 5, such that the heating elements 16a and b bear against and compress the dressing packs P. The switch 64 may be placed in the On position, resulting in heating of the dressing packs in the closed housing chamber 32. Thus, a plurality of dressings D are simultaneously heated to a precisely controlled temperature in the closed housing 12, and, after the dressings have been heated a sufficient length of time, the housing 12 may be opened to permit access to the heated wet dressings for use, if desired. Alternatively, with reference to FIG. 6, the heated dressings may be removed from the heating space 52 intermediate the heating elements 16a and b, and may be placed in the storage spaces 48a and b through the access openings 50a and b where the heated dressings are maintained at the desired temperature by the back side of the heating elements 16a and b. Thus, the dressings are maintained at the desired temperature in the storage spaces 48a and b until ready for use, with the insulation members 34a and b preventing heat loss from the housing both during initial heating of the dressings in the heating space 52 and during storage in the storage spaces 48a and b.

After placement of the heating dressings into the storage spaces 48a and b, additional dressings may be placed into the heating space 52 intermediate the heating elements 16a and b to permit the initial heating of further dressings while the stored dressings are maintained at the desired temperature. In this manner, a plurality of dressings may be simultaneously heated, and the heated dressings may be stored for subsequent use during heating of further dressings to provide a number of heated wet dressings which are available for simultaneous use on a patient. The dressings are then removed from the envelopes and may be placed on the patient, as needed, with the heating system 10 preventing overheating of the dressings which otherwise might cause discomfort and possible harm to the patient.

Another embodiment of a heating element for the heating system is illustrated in FIG. 7, in which like reference numerals designate like parts. In this embodiment, the heating element 16 has a pair of opposed covers 70 defining a cavity 72 to receive the central portion 74 of a heating conduit 76 which extends in a desired configuration throughout the cavity 72. One end portion 78 of the conduit 76 is connected to a source of heating fluid (not shown), such as heated water, and the fluid is circulated by suitable means through the central portion 74 of the conduit 76 after which the fluid returns through a second end portion 80 of the conduit 72 in order to supply heat to the element 16.

Another embodiment of a heating element for the heating system of the present invention is illustrated in FIG. 8, in which like reference numerals designate like parts. In this embodiment, the heating element 16 has a pair of opposed fluid impervious covers 70 sealed together at their edges to define a fluid receiving cavity 72. A first conduit 82 is connected between a source of heating fluid and the cavity 72, such that heated fluid is supplied through the conduit 82 to the cavity 72, and the fluid is returned through a second conduit 84 in order to circulate the heated fluid through the cavity 72 and supply heat to the element 16.

The foregoing detailed description is given for clearness of understanding only, and no unnecessary limitations should be understood therefrom, as modifications will be obvious to those skilled in the art.

We claim:

1. A heating system for dressings, comprising:

a housing having a pair of first and second closure shells, each of said shells having a back wall and sidewalls extending around the periphery of the associated back wall, with said back wall and sidewalls defining a cavity in each of said shells;

hinge means connecting a sidewall of said first and second shells and permitting movement of said shells between a first open position of the housing and a second closed position of the housing with the sidewalls of said shells mating and with said shells defining a closed chamber;

first and second elongated heating elements;

means for supporting said heating elements in the housing with said first heating element being located adjacent outer edges of the sidewalls in said first shell and substantially closing the cavity in the first shell, and with said second heating element being located adjacent outer edges of the sidewalls in said second shell and substantially closing the cavity in the second shell, said heating elements being closely facing each other in said second housing position to define a heating space intermediate the heating elements of the closed housing, and being widely spaced in said first housing position for receipt of the dressings intermediate the heating elements, said heating elements being at least partially free of attachment and defining an access opening adjacent an outer end of the respective shell relative said hinge means; and first and second insulation members in the housing, said first insulation member being located intermediate the first heating element and the back wall of said first shell and defining a narrow storage space intermediate the first heating element and first insulation member for placement of heated dressings through the associated access opening into the storage space, and said second insulation member being located intermediate the second heating element and the back wall of said second shell and defining a narrow storage space intermediate the second heating element and second insulation member for placement of heated dressings through the associated access opening into the respective storage space.

2. The system of claim 1 wherein said first and second heating elements contact each other in said second housing position.

3. The system of claim 1 wherein said first and second heating elements contact the associated first and second insulation member.

4. The system of claim 1 including means for releasably locking the housing in said second position.

5. The system of claim 1 including means for limiting movement of said first and second shells away from each other at said first housing position.

6. The system of claim 1 wherein said heating elements substantially close the cavities in the respective first and second shells.

7. The system of claim 1 wherein said supporting means permits expansion of the first and second heating elements away from the associated first and second insulation members to facilitate placement of heated dressings into the associated storage space.

8. The system of claim 7 wherein the supporting means comprises elastic means connected between outer edges of the first and second heating elements and the associated first and second shells.

9. The system of claim 1 wherein said heating elements comprise, first and second flexible heating pads having an outer cover, and an electrically conductive heating member extending substantially throughout said pads between the cover.

10. The system of claim 9 including means for controlling the electrical current passing through said heating members and the heat generated by said pads at a selected temperature.

11. The system of claim 10 wherein the heating members of said first and second pads are electrically connected together.

12. The system of claim 9 wherein said covers are made from a liquid impervious material.

13. The system of claim 9 including resilient pad means intermediate the covers of said first and second heating pads.

14. The system of claim 11 wherein said heating elements comprise a pair of opposed fluid impervious covers defining a fluid receiving cavity, and conduit means connected to the cavity for supplying heated fluid to the cavity.

15. The system of claim 1 wherein said heating elements comprise a pair of opposed covers defining a cavity, and conduit means extending throughout the cavity for circulating heated fluid between the covers.

* * * * *